US00PP14582P39

(12) United States Plant Patent
Yannai

(10) Patent No.: US PP14,582 P3
(45) Date of Patent: Mar. 9, 2004

(54) ***AERVA JAVANCIA* PLANT NAMED 'DESERT YEARNING'**

(50) Latin Name: *Aerva javanica*
Varietal Denomination: Desert Yearning

(75) Inventor: Yitzhak Yannai, Moshav Hazeva (Arava Tichona) (IL), 86815

(73) Assignee: Yitzhak Yannai (IL)

( * ) Notice: Subject to any disclaimer, the term of this patent is extended or adjusted under 35 U.S.C. 154(b) by 86 days.

(21) Appl. No.: 10/007,401

(22) Filed: Nov. 5, 2001

(65) Prior Publication Data

US 2003/0088898 P1 May 8, 2003

(51) Int. Cl.[7] ..... A01H 5/00

(52) U.S. Cl. ..... Plt./226
(58) Field of Search ..... Plt./226

(56) References Cited

PUBLICATIONS

Flora of Somalia vol. 1 p. 161–163. Edited by Mats Thulin. Royal Botanic gardens Kew. 1993.*

* cited by examiner

*Primary Examiner*—Bruce R. Campell
*Assistant Examiner*—Annette H. Para
(74) *Attorney, Agent, or Firm*—Webb Ziesenheim Logsdon Orkin & Hanson, P.C.

(57) ABSTRACT

A new and distinct *Aerva javanica* plant with a tall stem and light grey-green leaves suitable for cut flower production.

3 Drawing Sheets

Classification: *Aerva javanica.*
Varietal denomination: 'Desert Yearning'.

BACKGROUND OF THE INVENTION

The present invention comprises a new and distinct cultivar of *Aerva javanica* known by the varietal name 'Desert Yearning'. A variety was discovered in the wild in the Arava Valley, Israel at 100 m below sea level. Seed from the wild variety were collected, germinated and grown to maturity in a cultivated area. The new variety was selected from a population of *Avera javanica* plants as having the following desirable characteristics:

1. Hardy and firm stem.
2. Stem length of at least 80 cm.
3. Convenient plant shape for harvesting.
4. Stable flower color.
5. Long shelf life of cut flowers.
6. Attractive, unsymmetrical flowering.

The new variety differs from its native female population (unpatented) as follows:

1. 'Desert Yearning' has an average plant height of 1.5–1.8 m, whereas the native female population has an average plant height of 0.3–1.2 m.
2. 'Desert Yearning' has an average inflorescence length of 0.2–0.35 m, whereas the native female population has and average inflorescence length of 0.1–0.2 m.
3. 'Desert Yearning' blooms year round, whereas the native female population blooms only in spring and summer.

The new variety is similar to its native female population in leaf size and shape and flower shape and structure.

No male parentage or similar cultivars to 'Desert Yearning' are known.

The new variety was first asexually reproduced by cuttings in June 1997 in Hatzeva, Israel. Continued observations from the vegetative cuttings have confirmed that the distinguishing features of the new variety remain stable and are retained through successive propagations.

DESCRIPTION OF THE DRAWINGS

The accompanying photographic drawings illustrate the new variety, with the color being as nearly true as is possible with color illustrations of this type.

DESCRIPTION OF THE PLANT

Figure 1:
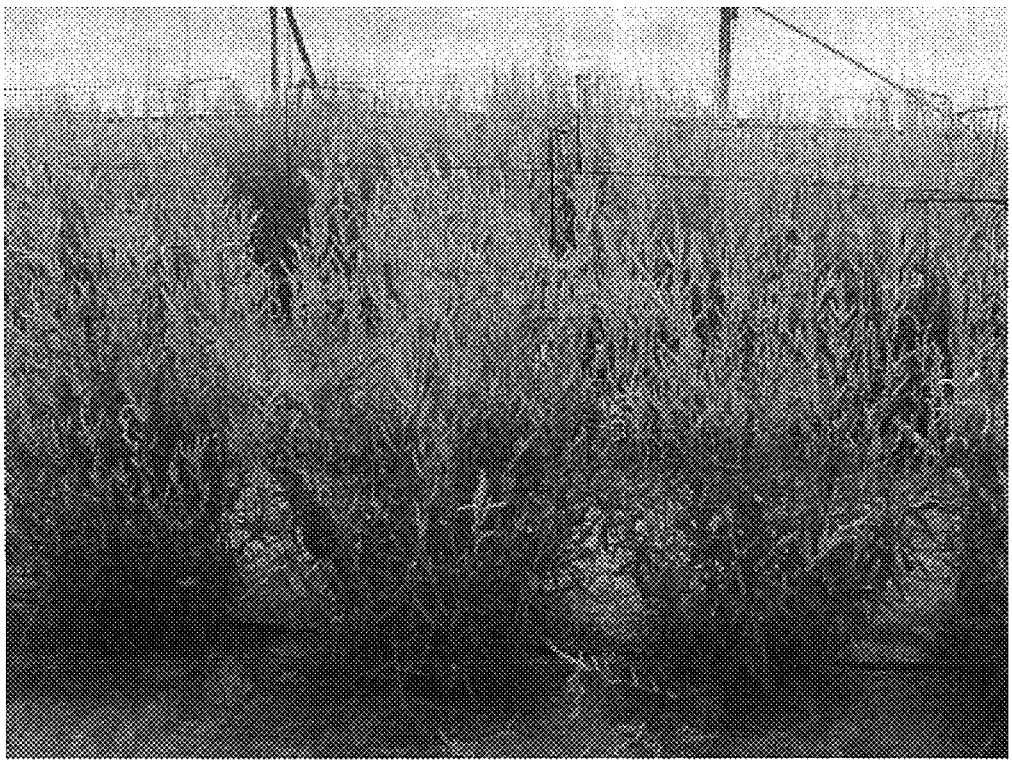
FIG. 1 illustrates multiple plants of the new variety.
Figure 2:
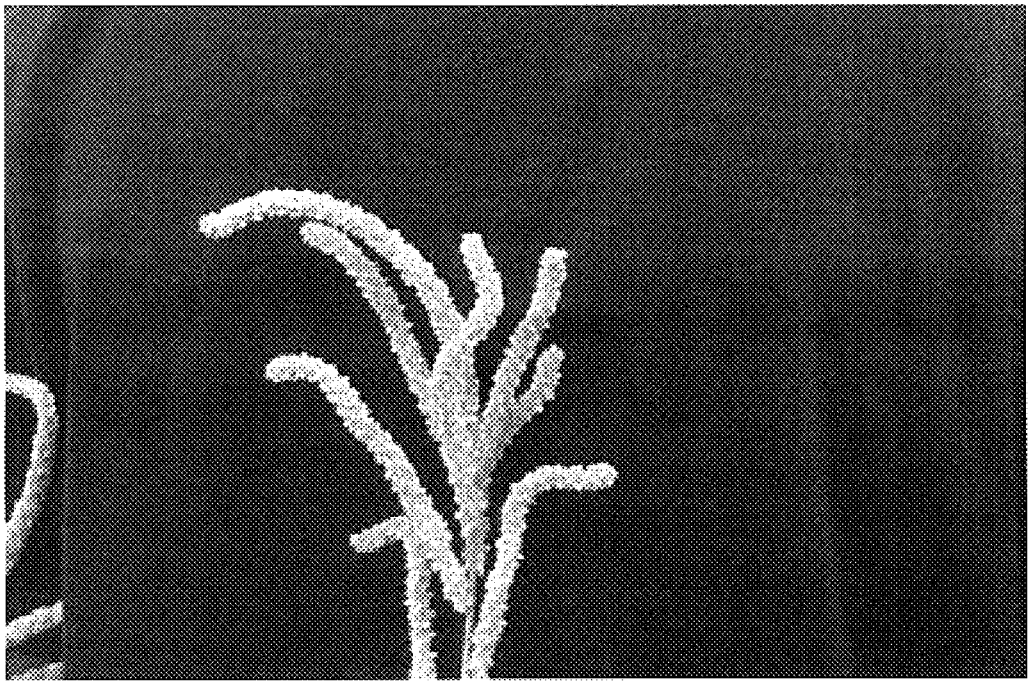
FIG. 2 is a close-up view of the inflorescences of the new variety.
Figure 3:
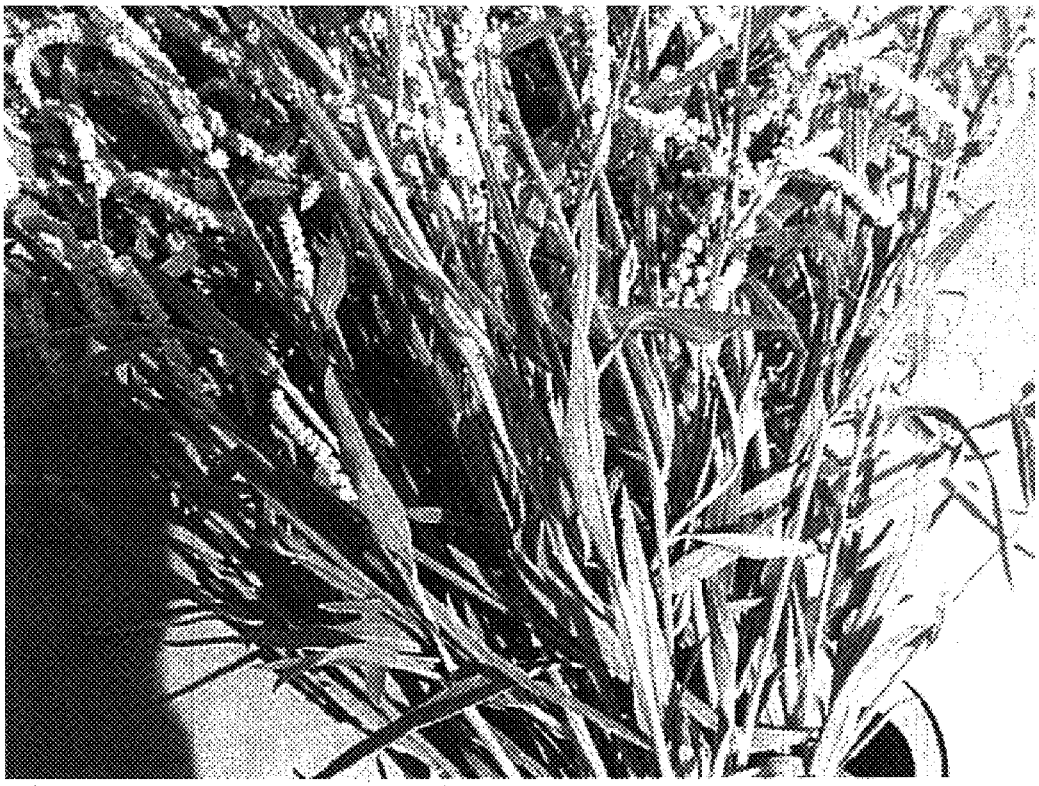
FIG. 3 is a close-up view of the foliage of the new variety.

The following detailed description sets forth the characteristics of the new variety. The data which defines these characteristics were collected by asexual reproductions by cuttings carried out in Hatzeva, Israel. Plants for the description were 2-years old. The new variety is an ornamental perennial shrub and grows well in sandy soils, open fields, or a greenhouse. Color references are primarily to The R.H.S. Colour Chart of The Royal Horticultural Society of London.

Plant:
Height: 1.5–1.8 m.
Width: 1.2 m.
Form: Erect.
Growth: Vigorous; fast growth rate.
Stem surface: Smooth texture, dull appearance.
Branches:
*Branching.*—Basal.
*Surface texture.*—Smooth; pubescent; no prickles.
*New growth color.*—196A.
*Mature growth color.*—196A.
*Length.*—Up to 1 mm.

*Internode length.*—60–70 mm.
*Cross-section.*—3 mm in diameter; solid.

Flowering stem:
*Length.*—1.2 m.
*Texture.*—Smooth.
*Diameter.*—4–6 mm.
*Internode length.*—60–80 mm.
*Color.*—196C.

Foliage:
*Arrangement.*—Opposite.
*Length.*—60–70 mm.
*Width.*—8–15 mm.
*Surface texture.*—Soft.
*Shape.*—Overall: Narrow; elliptical. Apex: Acute. Base: Acute. Cross section: Concave.
*Margin.*—Entire; undulating.
*Stipules.*—None.
*Color.*—Upper surface (young and mature): Green Group 138B. Lower surface (young and mature): Green Group 138C. Veins (upper and lower surface): Grey-green.
*Petioles.*—Length: 2–3 mm. Diameter: 1 mm. Color: Green Group 138D. Surface texture: Heavy pubescence.

Flowering: Naturally and continuously flowers in December — June in Israel. Numerous, small inflorescences colored White Group 157B. No fragrance. Year long flowering is achieved by growing the plant in a greenhouse covered with plastic (0.12 cm thick) with artificial daylight for 18 hours.

Reproductive organs:
*Anthers.*—Too small for observation.
*Pollen.*—Plentiful.
*Pistils.*—3 pistils 1 mm in length.
*Style.*—Length: 1 mm. Color: 177C.

Fruit:
*Shaped.*—Round.
*Texture.*—Solid.
*Size.*—1 mm.

Growing conditions:
*Winter irrigation.*—3–4 $m^3$ water with fertilizer per 1000 $m^2$ growing area per day.
*Summer irrigation.*—5–6 $m^3$ water with fertilizer per 1000 $m^2$ growing area per day.
*Fertilizer.*—150 ppm of 7-3-7.
*Cold tolerance.*—Below 8° C. inflorescences change color to brown.
*Drought tolerance.*—Strong; 'Desert Yearning' can last months without water; grows well even at temperatures of 40° C.
*Insect susceptibility.*—Sensitive to white fly.

I claim:

1. A new and distinct variety of *Aerva javanica* plant substantially as shown and described.

* * * * *